(12) United States Patent
Jacobsen et al.

(10) Patent No.: US 12,245,772 B2
(45) Date of Patent: Mar. 11, 2025

(54) SYSTEM AND METHOD TO CONTROL OPERATION OF A DRILL

(71) Applicant: Medtronic Navigation, Inc., Louisville, CO (US)

(72) Inventors: Brad Jacobsen, Erie, CO (US); Milton F. Barnes, Grand Prairie, TX (US); Rowena Vigh, Superior, CO (US); Steven Hartmann, Superior, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 402 days.

(21) Appl. No.: 17/556,299

(22) Filed: Dec. 20, 2021

(65) Prior Publication Data
US 2022/0192683 A1 Jun. 23, 2022

Related U.S. Application Data

(60) Provisional application No. 63/129,921, filed on Dec. 23, 2020.

(51) Int. Cl.
*A61B 17/16* (2006.01)
*A61B 34/00* (2016.01)
*A61B 34/20* (2016.01)
*G16H 40/63* (2018.01)

(52) U.S. Cl.
CPC ...... *A61B 17/1626* (2013.01); *A61B 17/1624* (2013.01); *A61B 34/20* (2016.02); *A61B 34/25* (2016.02); *G16H 40/63* (2018.01); *A61B 2034/2065* (2016.02)

(58) Field of Classification Search
CPC . A61B 17/1626; A61B 17/1624; A61B 34/20; A61B 34/25; A61B 2034/2065; A61B 17/1671; A61B 17/1695; A61B 2034/2051; A61B 2034/256; G16H 40/63; G16H 20/40
See application file for complete search history.

(56) References Cited

U.S. PATENT DOCUMENTS

| 106,825 A | 8/1870 | Hughes |
| 5,592,939 A | 1/1997 | Martinelli |
| 5,772,594 A | 6/1998 | Barrick |
| 5,913,820 A | 6/1999 | Bladen et al. |

(Continued)

FOREIGN PATENT DOCUMENTS

| CN | 101579250 A | 11/2009 |
| CN | 102046098 A | 5/2011 |

(Continued)

OTHER PUBLICATIONS

International Preliminary Report on Patentability, corresponding to PCT/US2021/064795, Date of Issuance: Jun. 13, 2023.

(Continued)

*Primary Examiner* — Juan M Guillermety
(74) *Attorney, Agent, or Firm* — Harness, Dickey & Pierce, P.L.C.

(57) ABSTRACT

Disclosed is a system and method for operating an assembly, such as a powered drill assembly. The assembly may be operated to provide feedback to the user regarding a selected position and/or condition of the powered drill system. The powered drill system may be used to power or drive a selected tool, such as a resection or grinding tool.

24 Claims, 8 Drawing Sheets

(56) References Cited

U.S. PATENT DOCUMENTS

| | | | |
|---|---|---|---|
| 5,983,126 | A | 11/1999 | Wittkampf |
| 6,940,941 | B2 | 9/2005 | Gregerson et al. |
| 7,001,045 | B2 | 2/2006 | Gregerson et al. |
| 7,001,391 | B2 | 2/2006 | Estes et al. |
| 7,011,661 | B2 | 3/2006 | Riedel et al. |
| 7,106,825 | B2 | 9/2006 | Gregerson et al. |
| 7,108,421 | B2 | 9/2006 | Gregerson et al. |
| 7,188,998 | B2 | 3/2007 | Gregerson et al. |
| 7,697,972 | B2 | 4/2010 | Verard et al. |
| 7,751,865 | B2 | 7/2010 | Jascob et al. |
| 8,238,631 | B2 | 8/2012 | Hartmann et al. |
| RE44,305 | E | 6/2013 | Foley et al. |
| 8,644,907 | B2 | 2/2014 | Hartmann et al. |
| 8,842,893 | B2 | 9/2014 | Teichman et al. |
| 9,241,771 | B2 | 1/2016 | Kostrzewski et al. |
| 9,283,048 | B2 | 3/2016 | Kostrzewski et al. |
| 9,737,235 | B2 | 8/2017 | Hartmann |
| 11,432,828 | B1 * | 9/2022 | Lang .................. A61B 17/142 |
| 2004/0199072 | A1 | 10/2004 | Sprouse et al. |
| 2006/0258951 | A1 | 11/2006 | Bleich et al. |
| 2007/0100336 | A1 * | 5/2007 | McFarlin ........... A61B 17/1622 |
| | | | 606/45 |
| 2008/0009697 | A1 | 1/2008 | Haider et al. |
| 2008/0242978 | A1 | 10/2008 | Simon et al. |
| 2010/0179557 | A1 * | 7/2010 | Husted ............. A61B 17/32002 |
| | | | 600/300 |
| 2010/0210939 | A1 | 8/2010 | Hartmann et al. |
| 2015/0305817 | A1 | 10/2015 | Kostrzewski |
| 2016/0235492 | A1 | 8/2016 | Morard et al. |
| 2018/0289432 | A1 | 10/2018 | Kostrzewski et al. |
| 2019/0269469 | A1 | 9/2019 | Bush, Jr. et al. |
| 2019/0328461 | A1 | 10/2019 | Kemp et al. |
| 2020/0178958 | A1 * | 6/2020 | Overmyer ............ A61B 17/068 |
| 2020/0237445 | A1 | 7/2020 | Snyder et al. |
| 2021/0298795 | A1 | 9/2021 | Bowling et al. |
| 2022/0192683 | A1 | 6/2022 | Jacobsen et al. |

FOREIGN PATENT DOCUMENTS

| | | |
|---|---|---|
| DE | 102017000723 A1 | 8/2018 |
| WO | 2016199152 A1 | 12/2016 |
| WO | 2017139674 A1 | 8/2017 |

OTHER PUBLICATIONS

International Search Report and Written Opinion regarding Patent Application No. PCT/US2022/023308, dated Sep. 2, 2022.

International Search Report and Written Opinion regarding International Patent Application No. PCT/US2021/064795, dated May 27, 2022.

Ronneberger, "U-Net, Convolutional Networks for Biomedical Image Segmentation", 2015 (Year: 2015).

Zhou, "Unet++: A cyclostyle u-net architecture for medical segmentation", 2018 (Year: 2018).

U.S. Appl. No. 17/555,777, filed Dec. 20, 2021, Brad Jacobsen et al.

Chinese Search Report received by the Chinese Patent Office for related Chinese Patent Application No. 202180087083.0 dated Dec. 6, 2024, 28 pages.

* cited by examiner

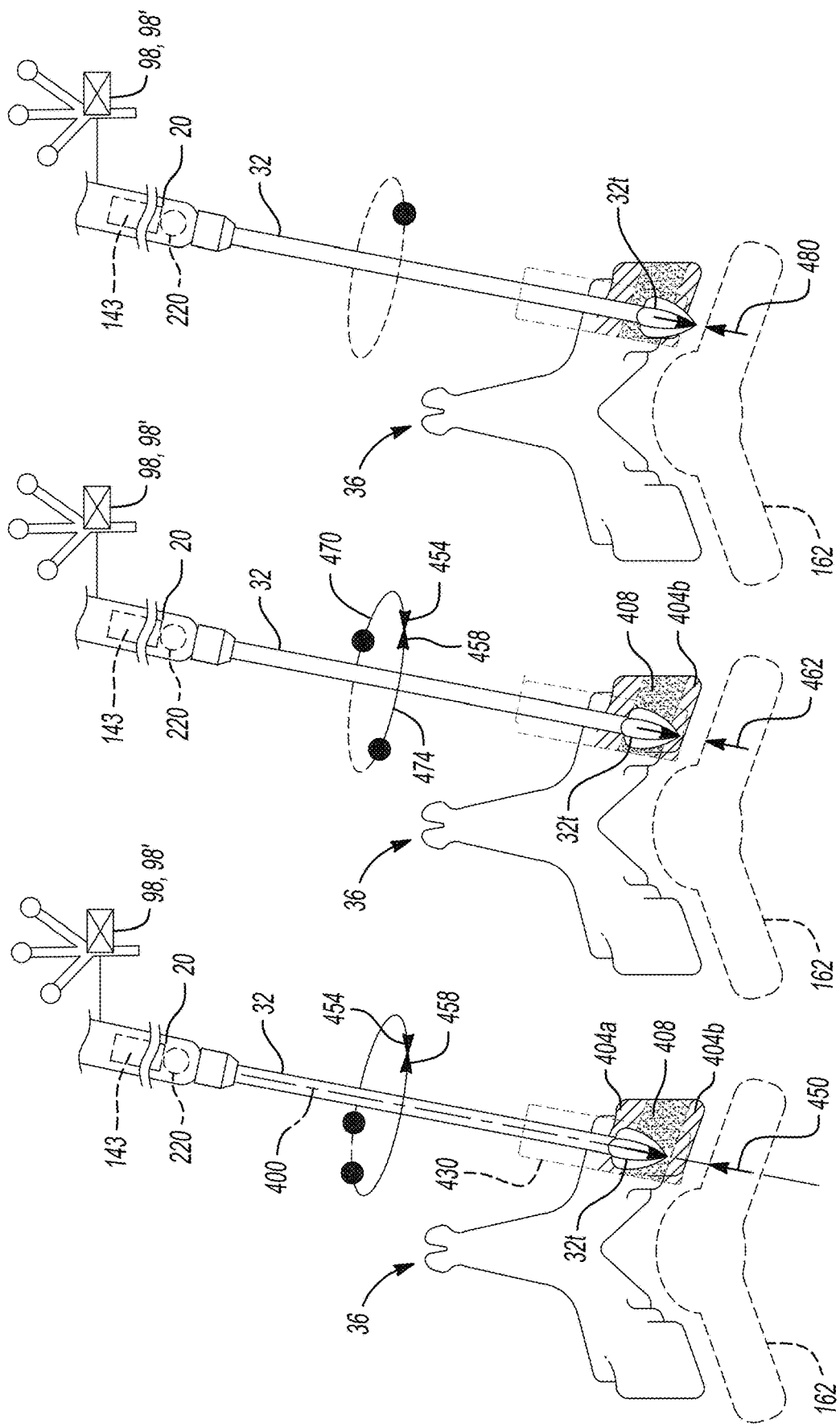

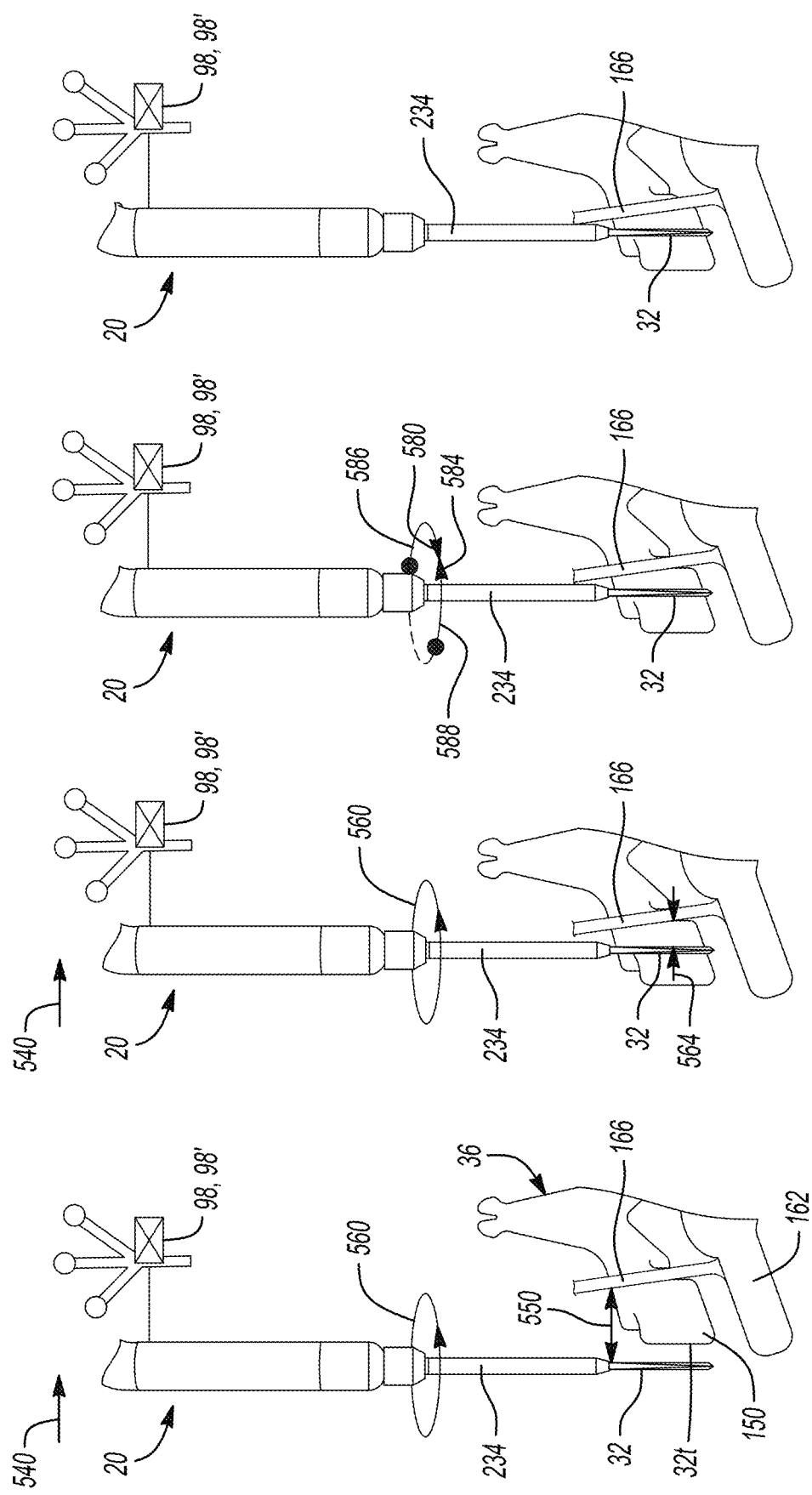

SYSTEM AND METHOD TO CONTROL OPERATION OF A DRILL

CROSS-REFERENCE TO RELATED APPLICATIONS

This application claims the benefit of U.S. Provisional Application No. 63/129,921, filed Dec. 23, 2020, entitled POWERED DRILL ASSEMBLY and this application includes subject matter similar to U.S. application Ser. No. 17/555,777, entitled POWERED DRILL ASSEMBLY. The entire disclosure of the above applications are incorporated herein by reference.

FIELD

The present disclosure relates to a powered drill, and particularly to a powered drill assembly with selected feedback.

BACKGROUND

During selected procedures, a motor may be operated to power a drill motor that moves a tool, such as a tool that has a tool tip or working end. For example, the tool may be rotated at a selected velocity, such as about 100 rotations per minute (RPM) to about 10,000 RPM. The tool interconnected with the motor may be connected to a drive shaft configured to be powered by the motor to rotate. A procedure may then be carried out with the rotating tool tip when powered by the motor.

During a selected procedure, such as a surgical procedure, the user of the tool (e.g. a surgeon) may need to rely solely on visual cues and experience for determining a location of the tool tip. During a procedure, at least a working end of a tool may be hidden from direct view or complete direct view of the user. Thus, an open experience may be required to properly perform a procedure.

SUMMARY

This section provides a general summary of the disclosure, and is not a comprehensive disclosure of its full scope or all of its features.

A powered drill may be provided to perform a procedure by a user. The powered drill may be powered in any appropriate manner, such as a pneumatic power, electrical power, or other appropriate power system to rotate at selected and/or selectable speeds including about 100 RPM to about 100,000 RPM, including about 75,000 RPM. The powered drill may power a tool for performing a procedure on a selected object, such as a human patient, or other appropriate subject or non-human object. The powered drill may be powered to rotate the tool, such as for drilling, forming a burr hole, or the like.

During the procedure, the subject may have a predefined location or portion for having a procedure performed thereon. For example, a skull of a patient may be selected to have a burr hole formed therein. The location, size, etc. of the burr hole may be predefined during a planning procedure. The selected procedure area or volume, however, may also be selected during a procedure. The power drill may be operated to form the burr hole in the selected portion of the subject.

The powered drill may also be operated to perform other procedures. For example, the powered drill may be operated to perform a spinal procedure. In various embodiments, vertebra resection for fusion and/or disk replacements may be operated.

The powered drill may be operated and/or controlled to provide feedback to a user during the use of the instrument. A navigation system may track the tool, such as a powered drill, power saw, and/or other appropriate item including a motor or power system that may be altered during its use to change a parameter, such as a cutting speed. Alternatively and/or additionally, sensors may be provided to sense motor power and/or stress. Further, a sensorless motor may be provide or used and other parameters may be sensed, such as a back reaction on the motor itself, for example the back electro-motive force (EMF) on motor coils, to determine motor operating properties.

The motor may be operated in selected and/or different manners to provide feedback, such as haptic feedback, to the user. Thus, a system may provide feedback to the user during operation of the powered drill. The feedback may be related to position of the tool, type of material being contacted by the tool, etc.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 5A through 5E are an environmental view of an operation of a system, according to various embodiments.

FIGS. 7A through 7D are an environmental view of an operation of a system, according to various embodiments.

Corresponding reference numerals indicate corresponding parts throughout the several views of the drawings.

DETAILED DESCRIPTION

Example embodiments will now be described more fully with reference to the accompanying drawings.

Figure 1:
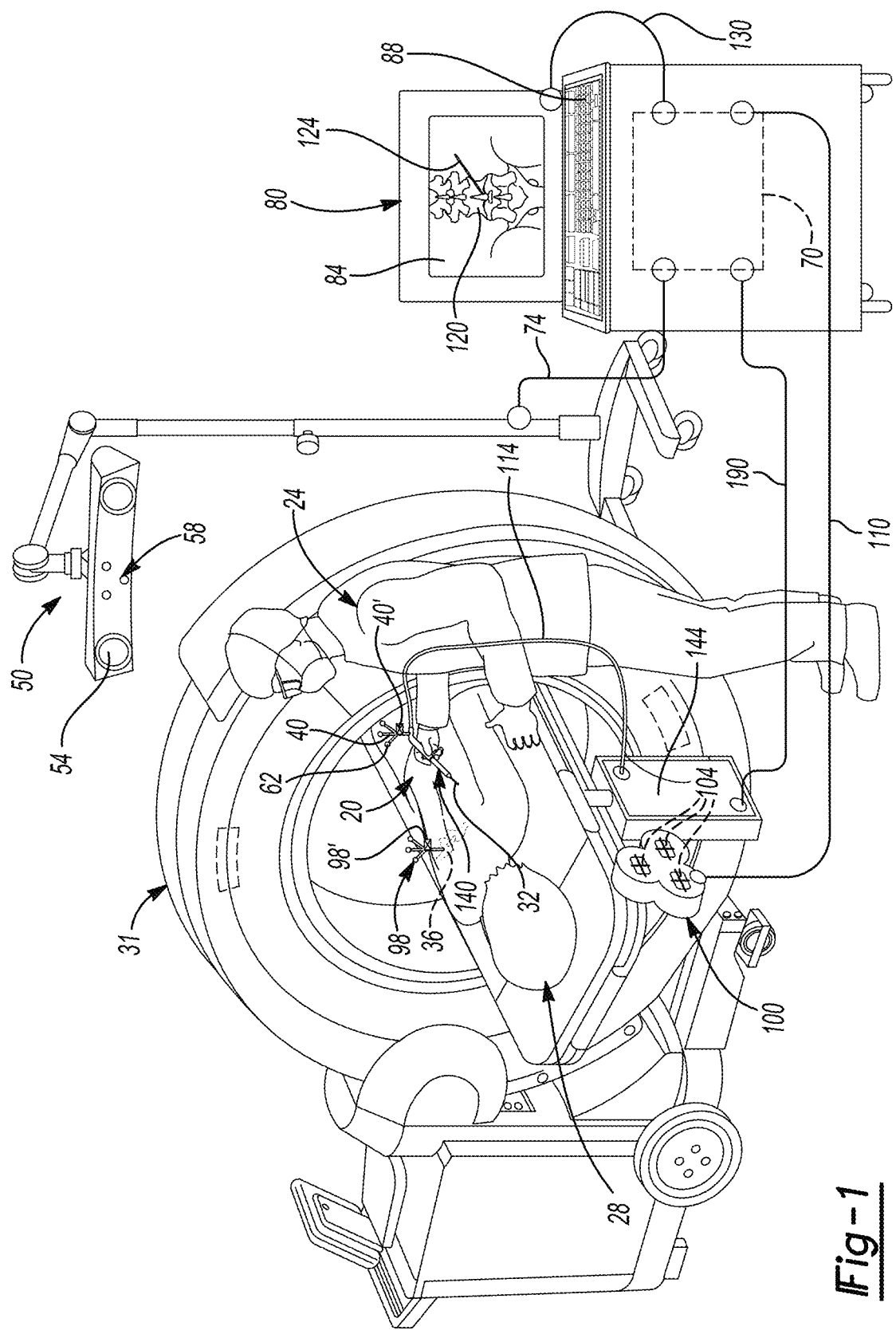
FIG. 1 is an environment view of a tracked motorized assembly.

FIG. 1 is an environmental view of an instrument, such as a powered drill assembly 20, being used by a user 24, to perform a procedure on a subject (e.g. a patient) 28. The powered drill assembly 20 may be powered to rotate a motor and/or a tool at selected and/or selectable speeds including about 100 RPM to about 100,000 RPM, including about 200 RPM to about 75,000 RPM. In various embodiments, the powered drill assembly 20 may include a powered dissection tool 32 for performing a select procedure, such as forming a burr hole in a cranium of the patient 28, operating on a vertebra 36, or other selected procedure. It is understood, however, that the powered drill assembly 20 may be used for performing other procedures such as a removal of material relative to and/or in the vertebrae.

For example, the powered drill assembly 20 may be operated to remove a portion of a vertebra in a selected procedure, including a laminectomy procedure or other appropriate spinal procedure. Further, it is understood that the powered drill assembly 20 may be used to perform a procedure on a non-living subject such as to drill a hole in an airframe, an automotive frame, or the like. Accordingly, the powered drill assembly 20 is not required to be used with a living subject, such as a human patient.

The powered drill assembly 20 may include a motorized drill that is tracked and/or navigated relative to the subject 28 according to various systems and/or procedures. For example, a tracking system, as discussed further herein, may include a tracking device 40 that may be connected to the powered drill assembly 20 to track a location of a tool relative to the subject 28, such as the vertebra 36. Appropriate tracking systems include those disclosed in U.S. Pat. No. 8,842,893, incorporated herein by reference. It is understood that image data may be acquired of the subject 28 to create images, as discussed herein. To acquire the image data, an imaging system 31 may be used prior to beginning a procedure or after a procedure has begun, the procedure may include operation of the powered drill 20. The imaging system 31 may include an O-arm ® imaging system sold by Medtronic, Inc. and/or may include those disclosed in U.S. Pat. Nos. 7,188,998; 7,108,421; 7,106,825; 7,001,045; and 6,940,941; all of which are incorporated herein by reference. Other possible imaging systems can include C-arm fluoroscopic imaging systems which can also generate three-dimensional views of the patient 28.

The tracking system may be a part of a navigation system to assist in performing selected procedures, such as a surgical procedure on the subject 28, and may include those as generally known in the art. For example, navigation systems may include those as disclosed in U.S. Pat. Nos. 5,772,594; 5,913,820; 5,592,939; 5,983,126; 7,751,865; and 8,842,893; and 9,737,235 and those disclosed in U.S. Pat. App. Pub. No. 2004/0199072, all incorporated herein by reference. Tracked locations may be displayed on images or relative to images due to registration of a location of a subject or real space to an image space, also as disclosed in the U.S. patents and publications as incorporated above. Further, tracking systems may include the Stealth Station® 58® tracking system, and AxiEM™ tracking system, all sold by Medtronic Navigation, Inc.

The tracking systems may include various features such as an optical tracking systems, EM tracking systems, ultrasonic tracking systems, or the like. Nevertheless, as illustrated in FIG. 1, for example, a tracking system may include one or more localizers that may include portions that include cameras and/or antennas for receiving/and or transmitting a signal for tracking. Localizers may include an optical localizer 50 that includes one or more cameras 54 that may detect or "view" the tracking device 40 connected to the power drill 20. The localizer 50 including the cameras 54 may emit a selected radiation, such as infrared radiation from emitters 58, that is reflected by one or more trackable portions 62 that are associated with the tracking device 40. The trackable portions 62 may be viewed by the cameras 54 and a signal may be transmitted to a navigation processor unit 70. The navigation processor unit 70 may include various features, such as a navigation probe interface (NPI), as discussed further herein. The navigation processor unit 70 may also include a coil array controller (CAC) for various types of tracking systems. Various features such as the NPI, the CAC, or other portions may be provided as separate units from the navigation processor unit 70 or separate modules for interacting with various portions of the navigation system, as is generally known in the art.

Nevertheless, the localizer 50 may communicate with the navigation processor unit 70 via a selected communication line 74. The communication line 74 may be a wired or a wireless communication with the navigation processor unit 70. The navigation processor unit 70 may communicate with a selected system, such as a workstation, a terminal, or the like that includes a display system or display module 80 having a display screen 84 and one or more user inputs 88. It is understood, however, that the display 84 may be separated for the processor unit 70 and/or in addition thereto, such as a projected display, a headset display (e.g., augmented reality systems). The user inputs 88 may include a keyboard, a mouse, a touch screen, or other tactical input. Further inputs may also include a foot switch, verbal inputs, visual inputs, or the like.

A subject tracking device 98 may also be connected, such as fixed, relative to the subject 28. In various embodiments, the subject tracking device 96 may be fixed to a vertebra. Generally, the subject tracking device is fixed relative to a selected portion of the subject 28.

In various embodiments, alternative or additional tracking systems may be provided, such as an electromagnetic tracking systems including an electromagnetic tracking array, such as a coil array 100. The coil array 100 may include one or more coil elements 104 that emit and/or receive an electromagnetic signal from an electromagnetic (EM) tracking devices, such as the subject tracking device 98 associated and/or connected to the patient 28 or a tracking device 40' connected to the power drill 20. The coil array 100 may communicate with navigation processing unit 70 via a communication line 110 similar to the communication line 74 from the localizer device 50 to the navigation processing unit 70. Further, each of the tracking devices may communicate with the navigation processing unit 70 via selected communication lines such as communication line 114 so that a position of the selected tracking devices, including tracking device 40 and tracking device 98 may be determined with a navigation processing unit 70. It is understood that one or more than one tracking system may be used simultaneously and/or serially during the selected procedure.

The display screen 84 may display an image 120 of a portion of the subject 28, such as an image of the vertebra 36. The image 120 may be based on or generated with image data acquired with the imaging system 31 as discussed above. Displayed relative to the image 120 and/or superimposed on the image 120 of the patient 28 may be a graphical representation, also referred to as an icon, 124. The icon 124 may represent a position such as a pose, of the powered drill assembly 20 that may include the tool 32, relative to the subject 28. The represented position may also be of only a portion of the assembly 20. The position of the powered drill assembly 20, or a portion thereof, relative to the subject 28 may be determined by registering the powered drill assembly 20 relative to the subject 28 and thereafter tracking the location of the powered drill assembly 20 relative to the subject 28.

Registration may include various techniques, such as those disclosed in U.S. Pat. Nos. RE44,305; 7,697,972; 8,644,907; 8,238,631; and 8,842,893; and U.S. Pat. App. Pub. No. 2004/0199072, all incorporated herein by reference. Generally, registration includes a mapping between the subject space and the image space. This may be done by identifying points in the subject space (i.e. fiducial portions) and identifying the same points in the image (i.e. image fiducials). A map of the image space to the subject space may then be made, such as by the navigation system. For example, points may be identified annually, automatically, or a combination thereof in the image data, such as in the image 120.

Related points may be identified in a subject space, such as defined by the subject 28. For example, the user 24 may identify a spinous process in the image 120 and an instrument tracked by one or more of the tracking systems, including the localizers 50, 100, may be used to identify a spinous process at the vertebrae 36. Once an appropriate number of points are identified in both the image space of the image 120 and the subject space of the subject 28, a map may be made between the two spaces. The map allows for a registration between the subject space defined by the subject, also referred to as a navigation space, and the image space defined by the image 120. Therefore, the instrument, or any appropriate portion, may be tracked with a selected tracking system and a poise of the instrument may be identified or represented relative to the image 120 with the graphical representation 124.

As discussed above, registration of the powered drill assembly 20 relative to the subject 28, such as with or to the subject tracking device 98, may be made at a selected point in a procedure. The image 120 may then be displayed on the display screen 84 and a tracked location of the powered drill assembly 20 may be displayed as the icon 124 relative to the image 120. The icon 124 may be superimposed on the image 120 to display a pose of at least a selected portion of the powered drill assembly 20, such as a distal end, of the tool 32 powered by the powered drill assembly 20. The pose may include a location that includes three degrees of freedom in space (for example, including at least one of a XYZ position) and a selected number (e.g., three) degrees of freedom orientation information location (for example, including at least one of yaw, pitch and roll orientation). The pose may be determined and/or calculated by the navigation processing unit 70 and communicated to the display device 80 via a selected communication line, such as communication line 130. The communication line 130 may be a wired or wireless or other appropriate communication line. Further, it is understood that the navigation processor unit 70 may include various features such as a selected processor (e.g., an application specific integrated circuit (ASIC), general purpose processor or the like). The navigation processor unit 70 may also include a memory system (e.g., non-transitory memory systems including spinning hard disks, non-volatile solid state memory, etc.) that includes selected instructions, such as those to perform the tracking, registration, superimposing of the icon 124 on the image 120, or the like. Therefore, the determined pose of the powered drill assembly 20 (for example the selected portion of the powered drill assembly 20, as discussed further herein), may be displayed relative to the subject 28 by the icon 124 relative to the image 120. The user 24 may then be able to view the display screen 84 to view and/or comprehend the specific pose of the selected portion of the powered drill assembly 20 relative to the subject 28 by viewing the display 84.

Figures 5A, 5B:
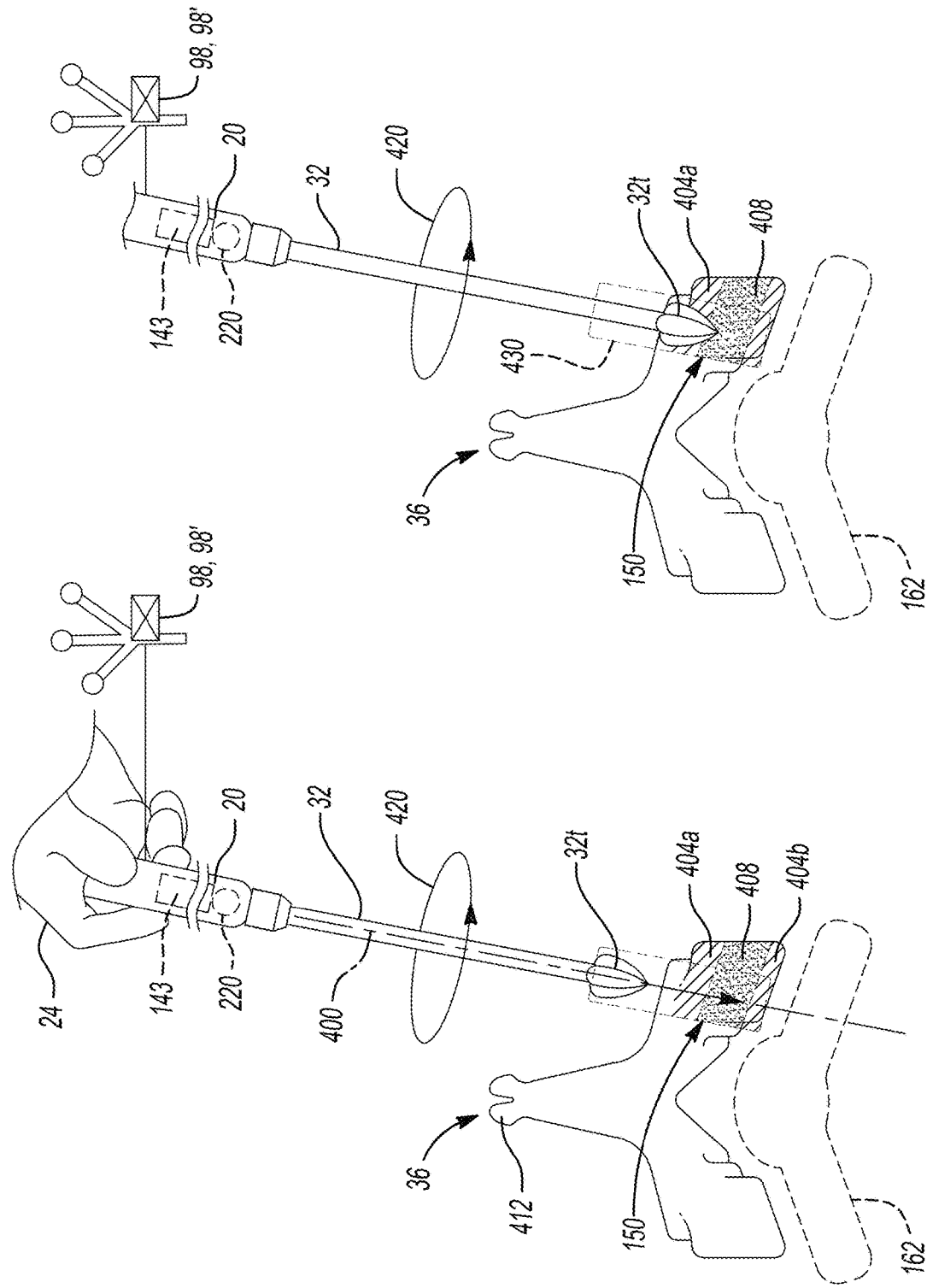

In various embodiments, the powered drill assembly 20 may include various components which may include a motor housing 140 of a motor assembly or component 143 (FIG. 5A). The drill 20 may include an appropriate motor component such as the LEGEND MR8® and/or LEGEND EHS STYLUS® motor systems, sold by Medtronic, Inc. The motor component may include a motor that is powered such as a pneumatic powered, such as the LEGEND MR7® motors although other power motors or drives may be used such as electric power motors LEGEND EHS STYLUS® motors.

The motor assembly may have a power and/or other signals transmitted to and/or from the motor assembly via the line 114 that is connected with a controller 144 that may also include a power source. The controller 144 may be any appropriate controller 144 such as the IPC® integrated power system, sold by Medtronic, Inc. It is understood, however, that the motor component may be any appropriate motor assembly such as one powered by electronic power, or other appropriate power supply. Therefore, the pneumatic power drill is not intended to limit the subject disclosure or the pending claims. Moreover, the motor component may include those disclosed in U.S. Pat. No. 7,011,661 or 7,001,391, both incorporated herein by reference.

Figure 2:
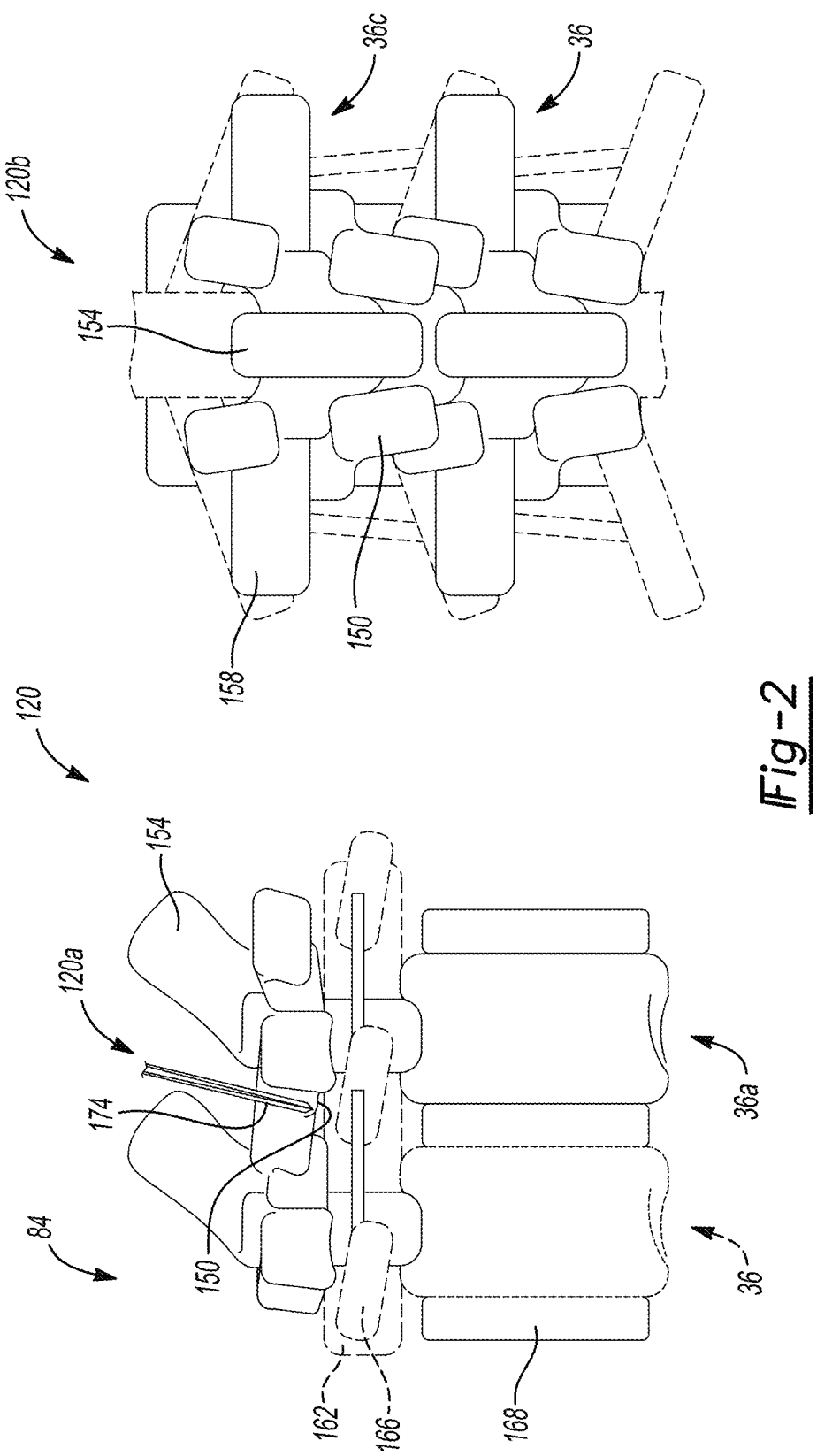
FIG. 2 is a schematic illustration of a portion of a spinal column from two directions.

As discussed above, a procedure may be performed on a subject 28. The procedure performed on the subject 28 may be performed with the drill assembly 20 having the instrument tool 32 extending therefrom. The drill assembly 20, as discussed above, may be navigated relative to the subject 28. In various embodiments, image guided procedures or image guided navigation may occur. Accordingly, the image 120 on the display screen 84 may include imaged portions of the subject 28. For example, as illustrated in FIG. 2, a medial-to-lateral (ML) (or vice versa) image portion 120a and a anterior-to-posterior (AP) (or vice versa) image view 120b may be illustrated on the display screen 84 as the image 120. The image 120, therefore, may include various portions, such as a first or ML view 120a and a second or AP view 120b. It is understood, however, that additional views or images may also be viewed for various purposes such as inferior to superior, or selected angles relative thereto.

In various embodiments, a portion of the image may be segmented for various purposes, such as planning a selected procedure. As discussed above, the drill assembly 20 may include the tool 32 for performing a procedure on the subject 28, such as a laminectomy, spinal decompression, intervertebral body fusion, or other selected procedures. A procedure may include moving the tool 32 to remove a selected portion of the subject 28, such as a selected portion of the anatomy of the vertebrae 36. The vertebrae 36 may include the first vertebrae 36 and a second vertebrae 36a, as illustrated in FIG. 2. The vertebrae may include various portions such as facets 150 or edges thereof, including a spinous processes 154. The vertebrae 36 may include portions that are included on each vertebrae such as the facet 150, the spinous process 154, and a transverse processes 158. In various embodiments, the facet and facet joint 150 may be resected a selected amount to perform a selected procedure, as noted above. However, during the procedure it may be selected to only have the tool 32 contact the portion of the vertebrae 36, such as at the facet 150. The vertebrae 36 is generally formed of bony material and may be resected by the tool 32.

Near or adjacent the vertebrae 36 may be non-bony tissue or soft tissue. For example, a spinal cord 162 of the subject may extend through the plurality of vertebrae 36. Further, various nerves or nerve roots 166 may extend from the spinal cord 162. The spinal cord 162, and the various nerve portions thereof, may generally be selected to not be resected during a selected procedure. Furthermore, one or more discs 168 may be formed between the various vertebrae 36.

The image 120 may be segmented to segment various portions such as the vertebrae portions 36, the spinal cord 162, and/or the nerve roots 166. For example, as illustrated in FIG. 2, the vertebrae may be segmented as vertebrae or bony portions and a graphical representation thereof may include illustrating the same with small dashes, a selected color, etc. The soft tissue or any appropriate portion, including the spinal cord 162, may be segmented and illustrated with large dashes, selected color, etc. It is understood that any appropriate identification may be made such as color, line weight, or the like. It is further understood that specific visual representations of the segmentation need not be made.

Further, segmentation of the image 120 may be formed in any appropriate manner, such as automatically, manually, or with manual input and automatic thereafter. For example, the user 24 may select an area or region (e.g. a pixel, a voxel, an area, etc.) and the system, such as the navigation processor 70, may execute selected instructions to segment the image 120. It is understood that a processing unit of any appropriate type may be used in addition to or in combination with a navigation processing unit 70. Therefore, various imaging processing, such as segmentation, need not be performed with the navigation processing unit 70. It is understood, however, that the processing units may be generally general processors and able to execute selected instructions for performing various tasks from a storage medium.

The image 120, whether segmented or not, may also be used to identify the plan for performing a procedure. Generally the plan may include various features or portions such as a plan region or volume 174. The plan 174 may include a trajectory, volume, or other portion that may be resected with the tool 32. Further, the plan may include a path to achieve the selected resection and/or the amount of resection. The plan may also include areas that are to be avoided or cautioned. For example, the spinal cord 162 may be identified as an area or region not to be contacted, penetrated, or accessed with the instrument 32.

The system, such as including the navigation processor 70, may automatically identify selected regions to be identified as avoided regions or volumes. Accordingly, the system may automatically segment and identify the spinal cord 162. Further, however, in addition or alternatively thereto, the user 24 may identify regions that are segmented in the image 120. Also, various regions to be avoided may be identified in the image 120 and saved for later access, such as during the procedure of moving the tool 32 relative to the subject 28.

In or with the image, regions to be avoided and/or regions for performing a procedure may be identified in the subject 28. The region to be avoided may be identified with a first instrument that is tracked. For example, a tracked/navigated pointer probe may be tracked to identify a volume in the subject space of the subject 28, such as relative to the vertebrae 36. The user 24 may move the tracked instrument to identify a region to be avoided and/or region to be operated on or for a procedure to be performed at a first time. Again, these regions may then be saved and recalled at a second time, such as after saving them, and during a procedure for providing selected feedback to the user 24.

Accordingly, during a selected procedure, the system, such as the navigation system, may be used to determine or provide feedback to the user 24 of the position of the tool 32 relative to selected predefined or saved regions, such as regions or volumes to be avoided. Further, the controller 144 for the power drill 24 may also provide selected feedback and/or receive signals from the power drill 20 and provide feedback based upon the saved and identified region that may be identified in the image 120 and/or in the subject 28, as discussed above. Further, the saved regions may be saved in a selected memory system, such as included with the navigation processing unit 70. The controller 144 of the power drill 20 may communicate with the processing unit 70, via a select communication line, such as the communication line 190. As discussed above, the communication line 190 may be any appropriate type such as a wired, wireless, or a combination thereof communication channel. Accordingly, the navigation processing unit 70 may communicate with the controller 144 for providing signals regarding the tracked or navigated position of the power drill 20 and/or signals from sensors associated with the power drill assembly 20.

Figure 3:
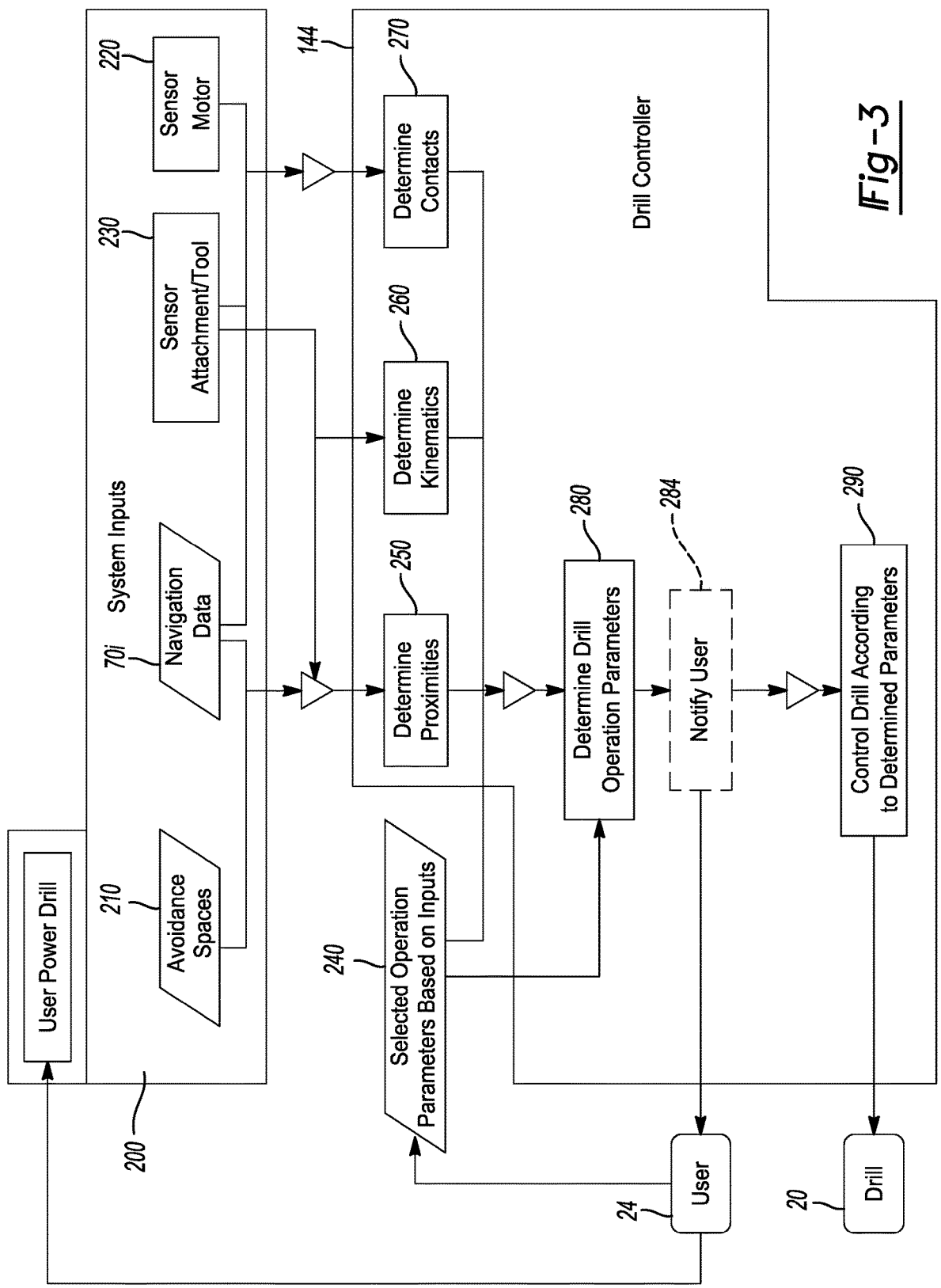
FIG. 3 is a schematic view of system and selected inputs and outputs, according to various embodiments.

With continuing reference to FIG. 1 and additional reference to FIG. 3, the drill assembly or instrument assembly 20 may be controlled by the drill controller 144, as discussed above. The drill controller 144 may include a processor module that may receive various inputs such as inputs 200. The inputs 200 may be processed according to selected instructions, as discussed further herein, to provide selected outputs to the user 24 and/or for operation of the drill assembly 20. It is understood that the drill assembly 20 is an exemplary instrument, and is discussed herein as an example of operation of a selected instrument, other instruments may include a powered saw, etc. Nevertheless, the drill assembly 20, as discussed above, may have a drill motor that is used to rotate the tool 32 for a selected procedure. As discussed above, the selected procedure may include resection or removal of a selected bone portion, such as a facet of the vertebrae 36. Accordingly, the following discussion exemplary describes removal of a portion or all of the facet 150 of the vertebrae 36 with the drill assembly 20 controlled by the drill controller 144 that may be in communication with the navigation processing unit 70.

Generally, as discussed above, selected inputs may be provided to the drill controller 144. As also discussed above, the drill controller 144 may include a selected processor and/or controls to control the operation of the drill assembly 20. It is understood, however, that the navigation processing unit 70 may also be used to control the drill assembly 20 and the controller 144 may simply allow for communication of the selected inputs and/or outputs to the drill 20. Nevertheless, the inputs 200 may provide input to the controller 144 to control the drill assembly 20.

The identified regions or areas or volumes to be avoided, as discussed above, may be identified as avoidance spaces or volumes 210. The avoidance spaces may also include caution zones. For example, an avoidance space may include a direct boundary of the spinal cord 162 and a caution zone may be a distance therefrom, such as 1 millimeters (mm), including about 0.5 mm to about 2 mm, etc. The avoidance spaces may be saved and recalled, such as with the navigation processing unit 70. The avoidance spaces or caution zone may be selected or determined to have selected distances that may vary depending upon an approach direction and/or pose of an instrument during or at the approach. For example, an anterior approach to an anatomical feature may include a 1 mm avoidance space while a posterior approach may include a 3 mm avoidance space. Thus, an avoidance space relative to a feature may vary depending upon a direction of an approach thereto. The direction and/or pose of the approach of an instrument may be determined with the navigation, as discussed herein. Accordingly, these inputs may be provided to the controller 144 for controlling the drill assembly 20. Further, during a selected procedure, tracking or navigation data 70i from the navigation processing unit 70 may also be input with the controller 144. The navigation data can include the determination of a pose of the drill assembly 20 and/or the tool 32 and/or a tool tip 32t. The tool tip 32t may include a working or distal end of the tool 32 and may be any appropriate tool tip. For example, the tool tip 32t may be a drill, a tap, a burr, or other appropriate tool tip.

In addition to the navigation data 70i from the navigation processor 70 and the identification of the avoidance spaces 210 as inputs, other selected sensors may also be provided to provide information regarding operation of the drill assembly 20. For example, a motor sensor 220 may be included in the drill assembly 20. The motor sensor 220 may include any appropriate type of sensor and may include a motor position sensor, include or provided to determine a back voltage or EMF from the motor of the drill assembly, etc. In various embodiments, the motor sensor 220 may include a voltage sensor regarding a back voltage or speed sensor of an actual speed of the tool 32 relative to an input voltage and/or selected input speed of the tool 32. Accordingly, the sensor 220 and/or a signal related thereto can provide information regarding the speed of the tool 32 relative to a selected input speed.

Additional tool or tool tip sensors 230 may also be provided. The tool tip sensors 230 may include an electrical sensor or continuity sensor 234 (see FIG. 7A-7D). The electrical sensor 234, as one of the sensors 230, may be any appropriate sensor for a nerve integrity monitoring system to sense continuity or an electrical signal being transmitted or transmitting a signal through a selected nerve, such as the spinal cord 162. The electrical sensor 234 may be part of a nerve integrity monitoring system (NIMS) and may provide input in sensing regarding proximity to the spinal cord 162, or other appropriate nerves. Appropriate NIMS may include the NIM® Nerve Monitoring Systems sold by Medtronic, Inc., such as the NIM 3.0 Nerve Monitor, the NIM-Response® 3.0, and NIM-NEURO® 3.0 monitoring systems all sold by Medtronic, Inc. Further, the sensors 230 may also include vibration, sound, or ultra-sound sensors that may sense vibration at or near the tool tip 32t, the tool 32, or other locations relative to the tool 32. The sensors 230, according to various embodiments, may also provide an indication of vibration and/or sound, force, and other parameters to be sensed near or at the working end 32t of the tool 32. Also, more than one sensor may be provided or several may be integrated into a single unit.

All of the input information 200 may be provided to the controller 144. Further, the user 24 may input various parameters 240. The selected operation parameters may include parameters such as selected feedback to the user 24, operation of the drill assembly 20, or other appropriate feedback or notifications of the user. Further, the parameters may include a distance from the avoidance spaces 210 to provide feedback and/or other operation of the drill assembly 20.

The drill controller 144 based upon the inputs 200 and the selected operation parameters 240 may make selected determinations and/or feedback or controls. Generally, the drill controller 144, may make a determination of proximities at block 250, determination of kinematics of the tool assembly 20 and/or the tool 32 at block 260, and determination of contacts in block 270. The determination of proximities 250 may be based upon selected information, such as the navigation information or inputs 70i from the tracking system including the navigation assembly or processing unit 70. The determination of kinematics in block 260 may also be based at least in part on the navigation data 70i, that may be used to determine speed, direction, etc. of movement of the drill assembly 20 and/or the tool 32. Further, the determination of contacts in block 270 may be determined or determining whether the tool 32, including the tool tip 32t, is contacting selected portions of the anatomy including selected bony portions. The determinations discussed further herein determined by the drill controller 144 illustrated in FIG. 3 is merely an exemplary illustration of the determination or operation of the system.

Nevertheless, the determinations by the drill controller 144 may further include determining the drill operation parameters in block 280. The determination of the drill parameters in block 280 may include selected operation parameters of the drill assembly 20, as discussed further herein. The determined operation parameters in block 280 may then be used to optionally notify the user in block 284. Notification of the user 24 in block 284 may include a visual indication on the display screen 84, an audio or audible signal, or other appropriate feedback, such as providing a haptic feedback with a haptic engine in the drill assembly 20. Accordingly, the user 24 may be provided feedback separate from the drill 20, such as with the display screen 84.

The drill controller 144 may also control the drill 20 according to the determined parameters in block 290. For example, the drill controller 144 may control the drill assembly 20, such as the motor of the drill assembly 20 in a selected manner as determined in the operation parameters from block 280. As discussed further herein, operation of the drill motor may include rotating the drill motor and the associated tool 32 at a selected speed, oscillating the tool 32 in a selected amount and/or selected speed, and/or ceasing operation of the drill motor on the tool 32. The user 24 may also be provided a feedback based upon an operation of the instrument assembly 20 controlled by the controller 144. Accordingly, notification to the user 24 may also be based upon operation of the drill assembly 20 and related operation of the tool 32.

The selected inputs 200 may be used to make selected determinations in the drill controller for operation of the drill assembly 20. The drill assembly 20 may then be operated based upon outputs from the drill controller 144, such as to control an operation of the motor of the drill assembly 20 and therefore the tool 32.

The controller, including the drill controller 144, may receive various inputs, such as those from user 24 and/or from various sensors, as discussed above. With continuing reference to FIGS. 1 and 2, and further reference to FIGS. 4-7D, operation of the instrument 20, which may include the drill motor, will be discussed. It is understood that the discussion herein is according to various embodiments, and that various disclosed features and inputs may be used in appropriate combination and/or without selected inputs, for operation of the instrument 20. The discussion of all the various sensor and inputs herein is for completeness of the current discussion, and is understood by one skilled in the art that various inputs and sensors may not be provided for operation of the instrument 20 with the controller 144.

Figure 4:
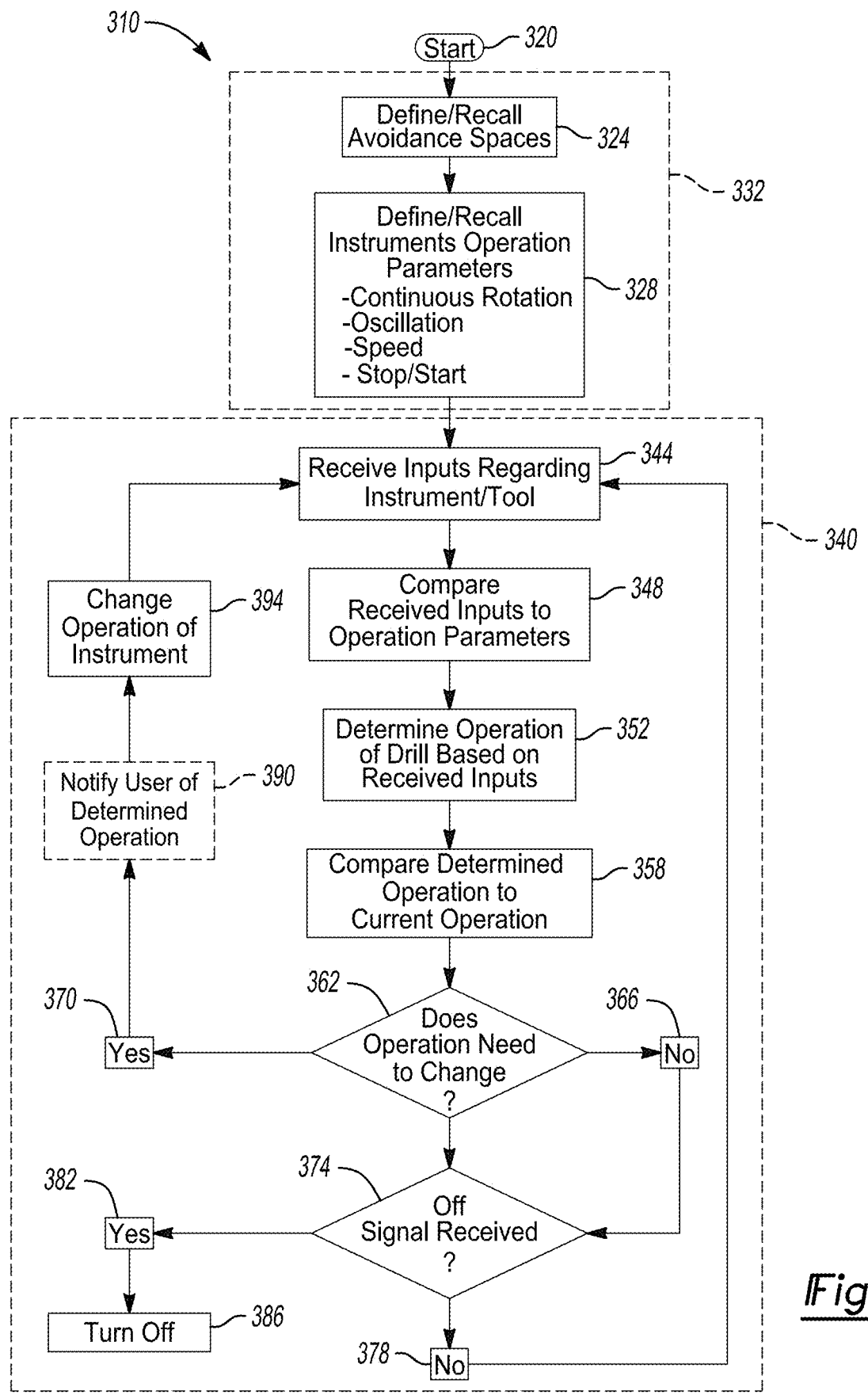
FIG. 4 is a flowchart of an operation of a system, according to various embodiments.

With initial reference to FIG. 4, a process or method 310 is illustrated. The process 310 may be carried out by a processor, such as the processor system 70 and/or processor included in the drill controller 144. The processor may be designed to carry out specific instructions and/or be a general processor that carries out specific instructions that are saved and recalled from a memory system. Nevertheless, the process 310 may be used to assist in operating the drill assembly 20 for controlling the tool 32 and/or notifying the user 24, as discussed further herein.

Generally, the process 310 begins at start block 320. The process 310 may then define or recall avoidance spaces in block 324. As discussed above, avoidance spaces may be those identified by the user 24, recalled according to predetermined restrictions or selections, or other appropriate mechanisms. As discussed above, in various embodiments, the image data and images may be segmented. The user 24 may then identify various portions of the segmented images and/or assist in the segmentation. For example, the user 34 may identify the spinal cord 162 and/or other portions, such as roots or nerves 166 extending therefrom. These portions may be visually identified in the image 120 and/or identified in a navigation space relative to the subject 28.

The definition or recalling of avoidance spaces may be used to determine operation of the drill 20, as discussed further herein. The system may also define or recall instrument operation parameters in block 328. The instrument operation parameters may include operation of the drill motor 20 for operation of the tool 32. In various embodiments, the tool 32 may be rotated continuously in a single direction, such as around the axis 420. Generally, the tool 32 may rotate around its axis or an axis at selected speeds. Accordingly, a selection of a continuous rotation and a speed may be determined and recalled based on various inputs, as discussed further herein.

Further, the tool 32 may be oscillated. That is the tool will rotate a selected amount in a first direction, then stopped, then rotated in another direction. For example, the tool 32 may be rotated in a first direction about 90 degrees from a start point and then stopped and rotated a selected amount, such as about 90 to about 180 degrees in the direction it originally came from. The tool 32 may then operated or controlled to continue to oscillate a selected amount, such as about 90 to about 180 degrees about its axis. It is further understood that the amount of oscillation may be changed and/or selected within a selected range such as about 1 degree to about 1500 degrees, including about 30 degrees top about 240 degrees, etc., of oscillation. In various embodiments, the amount of oscillation may include full rotations, such as one or even two full rotations (360 or 720 degrees) in one direction and then rotating the opposite direction a selected, such as the same, amount. The amount of oscillation may be selected for various purposes, such as to reduce drilling or material removal speed (e.g. moving, drilling, or moving through bone). Oscillation may also reduce the possibility and/or amount of tissue wrap, particularly compared to continuous one direction rotation. Further, the speed of oscillation may also be selected and used for operation of the tool 32. Further, the tool 32 may be stopped and/or started, such as to initiate or stop any of the other parameters of the drill motor 20 for operation the tool 32. As discussed further herein, the instrument operation parameters may be selected by the user 24 based upon or for when certain conditions are met. Accordingly, the user 24 may select an input in block 240 of parameters for operation of the drill 20. In various embodiments, the motor controller 144 may include preset or default parameters that the user 24 may select and/or a menu of operation parameters from which the user 24 may select. In various embodiments, however, the parameters may be entirely customized by the user 24, for various purposes.

The defining or recalling avoidance spaces in block 324 and the defining or recalling instrument operations in block 328 may be based upon initial operation or "set-up" of the operation of the drill 20 and it may be understood to be a preparation or recall phase block 332. The operation of the drill 20 may then be carried out by the motor controller 144 in operation block 340. The operation block 340 may include operation of the drill 20 according the parameter and receiving inputs to determine which parameters to apply to the drill operation of the drill and the associated tool 32.

In the operation block 340, the motor controller 144 may receive inputs regarding the instrument 20 and/or tool 32 in block 344. The receiving of inputs may include the inputs from block 200, as discussed above. Accordingly, the inputs may include the predetermined avoidance spaces in block 210 that may be recalled in block 324 and/or navigation data in block 70i. Other inputs may include the attachment or tool sensor in block 230 and the motor senor in block 220. Regardless the operation of the drill 20 based upon the inputs received in block 344 may be to alter or select an operation of the drill 20 when the user 24 has selected to power on or power the drill 20. Accordingly, the operation in block 340 may be after the user 24 has selected to operate or power the drill 20.

Based upon the received inputs or after receiving input in block 344 a comparison may be made to the operation parameter input in block 332. The operation parameters may include the avoidance spaces and caution zones, as discussed above, relative thereto in block 324 and the operation of the drill motor and tool in block 328. The comparison to the received inputs to the operation parameters may be determining whether the tool 32 is near or at an avoidance space, a determination of whether the drill is in a full rotation or oscillation mode, and/or other comparisons. As discussed further herein, for example, the tool 32 may be operated at a full rotation at a selected distance from the avoidance spaces and at an oscillation at a second distance (e.g., a caution zone) relative to the avoidance spaces. Accordingly, a comparison of the received inputs in block 348 to the operation parameters from block 332 may be made in block 348. After making the comparison in block 348, a determination of operation of the drill 20 may be made in block 352. As discussed above, the operation of the drill 20 may be based upon the selected inputs relative or compared to the defined parameters or other rotations, as discussed above. The drill 20 may be determined to be operated at a full rotation, oscillation, or other appropriate operation parameter as define in block 328.

After determining an operation of drill in block 352 a comparison of the determined operation to the current operation is made in block 358. The current operation may be a selected operation of the drill, such as the full rotation due to a prior input in comparison. In various embodiments, the inputs may be updated or checked at a selected frequency, such as once every second, ten times a second, once every millisecond, or any appropriate rate. Further, the update rate may change based upon a speed of the drill, such as based upon rotation speed and/or a travel speed determined by the navigation. Nevertheless, the comparison of the determined operation block 352 may be made to the current operation in block 358.

After the comparison in block 358, a determination of whether the operation of the drill needs to change in block 362 may be made. For example, if the comparison in block 358 finds a match between the determined operation and the current operation a determination block 362 then no change is determined to be needed and a NO path 366 may be followed. If, however, the comparison in block 358 finds that there is not a match between the determined operation and the current operation, a determination in block 362 may be that the operation of the drill does need to change and a YES path 370 is followed.

In operation, the determination in block 362 may be made by executing selected instructions and/or algorithms. In various embodiments, physics regarding motion and pose of the instrument may be considered and/or machine learning algorithms may be used to integrate several data sources and inputs for making the determination. Various situations may be detected via multiple sensors and use of machine learning to determine skiving and bone breakthrough. Thus, multiple data streams from the inputs or sensors 200 may and/or are used to determine drill operation. Navigation data 70i includes both tracking data (e.g., current and recent past tool positions and orientations) as well as imaging data (e.g. tool with respect to and within patient anatomies). One example is using navigation data 70i is used to determine kinematics via physics based algorithms 260, navigation data 70i and avoidance space 210 data to determine proximities 250 via physics and/or machine learning based algorithms. Further, all of these as well as system parameters 240 may be used to determine drill parameters via optimization and/or machine learning based algorithms 280. Additionally use navigation data 70i and motor sensing 220 and/or other sensing data 230 may be used to determine contacts 270 via physical, statistical, or machine learning algorithms. Also, again, all these things as well as system parameters may be used to determine drill parameters 280 via optimization or machine learning algorithms.

Accordingly, if the NO path 366 is followed, a determination of whether an off signal is received in block 374 may be made. If an off signal is not received (i.e. to stop operation of the drill 20) a NO path 378 may be followed to again receive inputs in block 344. Thus, the operation of the drill may be a loop until an off signal is determined to be received at block 374. Accordingly, if a received off signal is received in block 374, a YES path 382 may be followed and operation of the drill may be ceased or it may be turned off in block 386.

As discussed above, the determination block 362 may be that the determined operation does not match the current operation. Thereafter, a YES path 370 may be followed. In following the YES path 370, a notification to the user 24 that the operation of the drill 20 will change may optionally be made in block 390. The notification of the user 24 that the operation of the drill 20 will change may be a visual indication, such as displayed on the display screen 84, an audible notification, a haptic or touch sense of feedback, or other appropriate notification. The notification to the user in block 390 may identify or indicate to the user 24 that operation of the drill 20 will change at a selected time, such as immediately, after a selected period, or the like.

Changing operation of the instrument or the drill in block 394 may then follow. As discussed above, the drill 20 may be operated in a selected or according to a selected operation parameter, such as those recalled in block 328. Accordingly, if a determination is made that the comparison of the determined operation and the current operation does not match, the YES path 370 may lead to changing operation of the instrument in block 394. In various embodiments, as discussed further herein, the change of operation may be from a full rotation to an oscillation, a change in speed (e.g., increase or decrease in speed), or other change in operation of the instrument or drill in block 394. After changing operation of the drill in block 394, the operation process 340 may again loop to receive inputs in block 344.

Accordingly, the drill 20 may be operated according to the process 340 in a substantial loop manner until a signal to turn off the drill is received. The signal may be a manual signal from the user 24, such as with a foot switch, hand switch, or other appropriate switch. Other off signals may also include an off signal to cease operation of the drill after a selected period of time, a selected distance of movement, or the like.

With continuing reference to FIGS. 3 and 4, and additional reference to FIGS. 5A, 5B, 5C, 5D, and 5E, in various embodiments the drill 20 may be operated to operate or move the tool 32, such as its tip 32t relative to various portions of the subject 28, such as the vertebrae 36. The drill 20, or any appropriate portion of the instrument 20 may be held by the user 24. It is understood, however, that the drill 20 may also be held or positioned with a selected mechanism, such as a robotic system (e.g., Mazor X Stealth Edition® robotic assisted surgical systems sold by Medtronic, Inc.) that may hold, control, and/or move the drill 20 in a selected direction, such as substantially axially along an axis 400 of the tool 32. The tool 32, such as with the drill 20, however, may also be held with a substantially rigid member or the like for operation or movement or holding of the tool 32. As discussed herein, the tool 32 may rotated about the axis 400 (and/or a line generally parallel thereto) and/or oscillate about the axis 400 (and/or a line generally parallel thereto).

The tool 32 may be operated according to a selected operation parameter, as discussed above for performing a selected procedure. For example, the tool 32 may include the tool tip that may be operated to remove a selected portion of the vertebrae 36, such as a portion or all of the facet 150. The vertebrae 36 may include various types of bone portions such as a cortical bone portion 404 that is formed at or near an exterior of the bone facet 150 and a cancellous bone portion 408 that may be formed within the bone relative to the cortical bone 404, such as near an interior of the bone 36. Accordingly, the cortical bone portion 404 may include a first cortical bone portion 404a and a second cortical bone portion 404b. As illustrated in FIG. 5A, the first cortical bone portion 404a is near a spinous process 412 of the vertebrae 36 and substantially posterior relative to the subject 28. The second cortical bone portion 404b is, therefore, near the spinal cord 162 and more anterior to the subject 28. It is understood, however, that the cortical bone portions 404 may surround the cancellous bone portions 408 in the bone, such as the vertebrae 36.

Generally, the cortical bone 404 is denser than the cancellous bone portion 408. Thus, a greater force, such as a greater torque, may be required to remove or drill through the cortical bone 404 than the cancellous bone 408. As discussed further herein, therefore, the motor sensor 220 may sense operation of the motor 143 for operation of the tool 32 that may vary due to the different bone portions or bone types, such as the cortical bone 404 and the cancellous bone 408. Given the differences in the bone, moving through the cortical bone slowly may require a lesser torque and the cancellous bone more quickly may require a greater torque. These conditions and operating parameters may be useful for operation. For example, combining navigation and motor data can determine contact type more reliably than navigation or motor data alone.

During movement of the tool 32 relative to the vertebrae 36, such as through the cortical bone 404 and/or the cancellous bone 408 toward the and/or relative to the spinal cord 162, the navigation system may track the tracking device 98, 98' relative to the tool 32 and/or the drill 20. During operation of the tool 32, the drill 20, including the motor 143, may power the tool 32 and move the tool 32 relative to the vertebrae 36. The tracking device 98, 98' may be used to determine a position of the tool 32 relative to the vertebrae 36 and/or the spinal cord 162. As discussed above, the boundary of the spinal cord 162 and/or a boundary of the vertebrae 36 may be used to define various avoidance spaces or volumes.

During selected positions of the tool 32 relative to selected avoidance spaces, such as at or near the spinal cord 162, the tool 32 may be operated by the motor 20 for a substantially full rotation manner, as illustrated by a circle 420, generally or substantially around the axis 400 or a line generally parallel thereto. In full rotation at a selected speed, such as a maximum speed, the tool tip 32t may move through the bone, such as the facet 150, at a selected maximum rate. Accordingly, the cortical bone 404a and the cancellous bone 408 may be drilled through at a selected speed. Further, the tracking device 98, 98' may be used to determine the positon of the tool tip 32t relative to any appropriate portion of the image data, such as the spinal cord 162. Thus, as discussed above, during a selected determined (e.g., navigated) position of the tool tip 32t (such as at distances away from the avoidance spaces) which may include boundaries of the spinal cord 162, the drill 20 may be operated at a maximum rotational speed for efficient and quick drilling or movement through the facet 150.

During operation of the drill 20, the tool 32 having the tool tip 32t may engage the cortical bone 404 and the cancellous bone 408. The cortical bone 404, due to it being harder, may cause a greater resistance on the tool tip 32t. Accordingly, the motor sensor 220 may sense a first back voltage from the motor regarding the additional force required to rotate the tool 32 at a selected or determined speed or rotation of the tool 32. The motor sensor 220 may also sense a second back voltage when the tool encounters the cancellous bone 408, which may be less dense than the cortical bone 404, and the speed of the tool 32 may be easier to achieve. Thus, at least two or different back voltages may be sensed that may be due to different bone being encountered by the tool 32. As discussed above, the motor may also operate in a sensorless manner where the motor may itself be used to determine back EMF for control of the motor.

Further, the position of the tool 32 and the tool tip 32t may be tracked and determined with the selected tracking device 98, 98'. As is generally understood by one skilled in the art, the tool tip 32t may have a known distance from the tracking device 98, 98' which may be connected to the drill 20. Accordingly, as the drill 20 moves, the tracking device 98, 98' may move and the position of the tool tip 32t may be known.

As illustrated in FIG. 5A, the tool tip 32t may be positioned a distance from the facet 150. As illustrated in FIG. 5B, however, the tool tip 32 may engage the facet 150. As the tool tip 32t engages the facet 150 it may initially engage the cortical bone 404a. The tracking device 98, 98' may track the position of the tool tip 32t and the navigation system may determine and/or display the position of the tool tip 32t. As the tool tip 32t is at the cortical bone 404a, and a selected distance away from the spinal cord 162, the tool 32 may be selected to rotate in a selected direction and/or speed, as discussed above. Accordingly, when the tool tip 32t is a selected distance away from the spinal cord 162, or other selected avoidance zone or area, the tool 32 and the associated tool tip may be rotated at a selected speed, which may be selected by the user 24.

Further, the tool 32 may be rotated at a selected speed with no alteration thereof, as long as the tool 32 is in a selected planned position. As illustrated in FIGS. 5A and 5B, a plan 430 may be identified relative to the facet 150. The plan 430 may include a geometry or volume or trajectory of the tool 32, including the tool tip 32t. Thus, as long as the tool 32 is in a selected position, such as within the planned volume or area 430, and a selected distance from the avoidance areas, including the spinal cord 162, the tool 32 may rotate a selected speed and/or direction or type, such as in the direction of 420. Accordingly, the tool 32 may continue to operate in a full rotation and at a selected speed when navigated at a selected part of the plan. Further, the sensor 220 may sense a back voltage to the motor to assist in determining that the tool tip 32t is in or passing through the cortical bone 404a.

With reference to FIG. 5C, the tracking device 98, 98' can be used to determine or navigate a position of the tool tip 32t. As illustrated in FIG. 5C, the tool tip 32 may be within the planned trajectory 430, but also a selected distance or determined distance 450 from the spinal cord 162, which may be determined to be an avoidance space. Accordingly, the drill 20 may operate to oscillate the tool 32, generally or substantially around the axis 400 or a line generally parallel thereto. In oscillating the tool, the tool 32 may rotate a first distance in the direction of arrow 454, stop, and then rotate a second distance in the direction of the arrow 458. The two arrows, as illustrated in FIG. 5C, may be opposed to one another to illustrate an oscillation of the tool 32.

The distance 450 may be a selected distance from the spinal cord 162 such that the operational parameters, as discussed above, may allow a large oscillation. As illustrated in FIG. 5C, the oscillation may be about 280 degrees to about 360 degrees around the axis 400 of the tool 32. Accordingly, a large oscillation may still allow for efficient or quick cutting of the vertebrae 36, however, with more control and/or feedback to the user regarding a tracked position of the tool 32.

Further, as illustrated in FIG. 5C, the tool tip 32 may be positioned within the cancellous bone 408. Accordingly, the motor sensor 220 may sense a back voltage for operation of the motor. The motor sensor 220 may be used to sense the torque applied to the tool tip 32t to move through the bone and further assist in determining a position of the tool tip 32 relative to the vertebrae 36 and/or the spinal cord 162. As discussed above, various portions of the anatomy may be determined and/or segmented and therefore the type of bone relative to the spinal cord 162 may be determined and known. The tracked position of the drill 20, and the related tool 32, may be used to determine a position relative to the avoidance space in addition and/or alternatively to other sensors, such as the motor sensor 220, which may be used to assist in determining or sensing the type of bone being counted.

Turning reference to FIG. 5D, the tool tip 32t has moved closer to a distance 462 from the spinal cord 162. The tracked or navigated position of the tool tip 32t may be determined with the tracking device 98, 98'. The distance 462 may be a selected distance to further alter operation or rotation of the tool 32. As illustrated in FIG. 5D, the tool tip may continue to oscillate in the direction as illustrated by the arrows 454, 458, but in a smaller oscillation, generally or substantially around the axis 400 or a line generally parallel thereto. As illustrated in FIG. 5D, for example, the oscillation of the tool may include an arc that equals less than the total arc illustrated in FIG. 5C. For example, the oscillation in the direction of arrow 454 may be along an arc 470 that is about 50 degrees to about 120 degrees, including about 90 degrees. Further, the oscillation in the direction of the arrow 458 may be along an arc 474 that may be a selected distance, such as about 50 degrees to about 120 degrees, and including about 90 degrees. Thus, the oscillation illustrated in FIG. 5D when the tool tip 32*t* is the distance 462 from the avoidant space, such as the spinal cord 162, may be less than the oscillation when the tool tip 32*t* is the distance 450 from the avoidance space. As illustrated in FIG. 5D, for example, as the tool tip 32 is closer to the avoidance space, the oscillation of the tool 32 may be reduced. Further, the speed of the oscillation may be reduced. Accordingly, the user 24 may receive feedback due to the operation of the drill 20 regarding a position of the tool tip 32*t* relative to the avoidant space.

With reference to FIG. 5D, the tool tip 32 may enter or be entering the cortical bone 404*b*. As discussed above, the motor sensor 220 may sense the high voltage to the motor when the tool tip 32*t* encounters the cortical bone 404*b*. The change from the cancellous bone 408 to the cortical bone 404*b* may be determined or sensed with the motor sensor 220. Accordingly, both the tracked position with the tracking device 98, 98' and the sensing of the motor operation by the motor sensor 220 may be used to assist in determining a position of the tool tip 32*t* relative to the avoidance space, such as of the spinal cord 162.

Finally, as illustrated in FIG. 5E, the tool tip 32 may pass through the vertebrae 36. The tool tip 32*t*, therefore, may be a distance 480 from the spinal cord 162, which may be the avoidance space. In this position, the tool 32 may be stopped such that the tool 32 does not rotate any longer. The position of the tool tip 32*t* may be determined based upon the tracking of the tracking device 98, 98'. Further, the motor sensor 220 may be used to sense that the tool is no longer engaging or encountering as much resistance wherein the tool tip 32 passes through or partially passes through the vertebrae. Therefore, the sensor 220 may also provide sensing of operation of the motor 143 to assist in determining the position of the tool tip 32*t*.

Thus, the tool 32 may be used to perform a procedure. The tracked position of the tracking device 98, 98' may be used to determine the position of the tool tip 32*t*. Based upon the tracked position of the tool tip 32*t*, the motor of the drill 20 may be operated to allow for full rotation at a selected speed, oscillate a selected amount, reduce oscillation, and/or stop operation of the motor and the tool 32. This may provide feedback to the user regarding position of the tool tip 32*t* and/or assist in efficiently or effectively drilling through the vertebrae 36, or a selected portion of the subject 24, while having feedback and operation of the tool 32 based upon predetermined selected spaces or volumes.

As discussed and illustrated in FIGS. 5A-5E, an exemplary application, according to various embodiments, of the inputs and operation of the drill 20, as illustrated in FIG. 3, and the process 310, as illustrated in FIG. 4, is included. As discussed above, various operation parameters of the drill 20 may be initially input or recalled. Based upon tracking and determining the position of the tool 32 and/or the tool tip 32*t*, the drill 20 may be operated to change a speed, direction, rotation and/or oscillation, or stop. Thus, the drill 20 may be operated according to a predetermined and/or recalled tool operation parameters based upon a tracked or determined position of the drill 20 and/or the tool 32 and/or the tool tip 32*t*. Additionally, sensors, such as the motor sensor 220 may be provided to include or provide additional inputs for operation of the drill 20. The drill 20, therefore, may be operated based upon the input parameters and tracked position and/or sensed operation of the motor.

Figure 6:
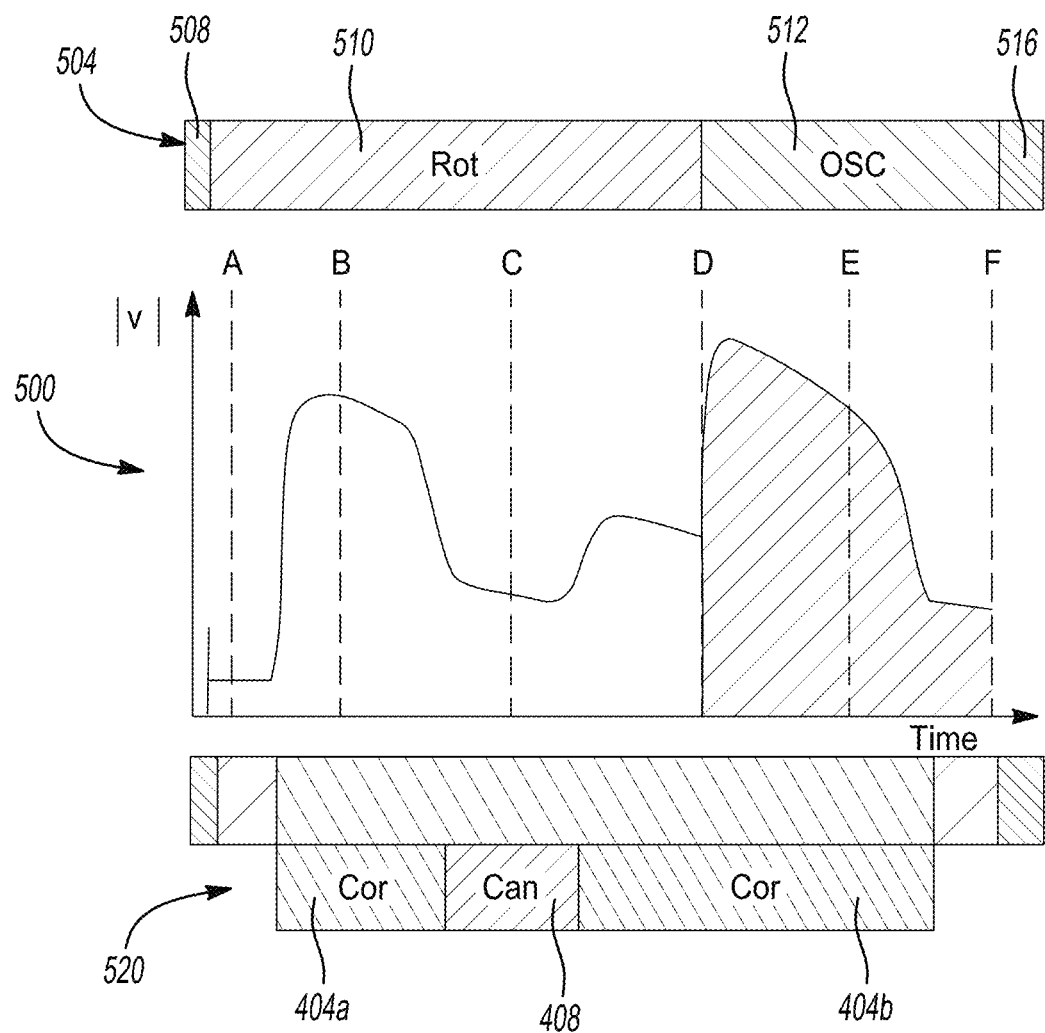
FIG. 6 is a graph illustrating operation of a system based on input from various sensors, according to various embodiments.

As illustrated in FIG. 6, for example, the drill 20 that may include the electric motor 143 that operates based upon the position of the tool tip 32*t*, relative to the subject. FIG. 6 illustrates a graph 500 of operation of the drill 20, relative to the tool 32 and the vertebra 36. The Y-axis indicates a voltage sensed by the motor sensor 220 and the X-axis shows time. Additionally, a top bar 504 illustrates a change in type of rotation or movement of the tool 32 over time. Accordingly, as discussed above, the tool 32 may have an initial stop or start up at 508, rotate, such as in the direction of the arrow 420, at time 510, oscillate, as discussed above, at time 512, and again stop at 516. The graph illustrates the change in voltage sensed by the motor sensor 220 that may correlate to the different types of rotation as illustrated in the row 504.

The bottom bar 520, along the Y-axis, illustrates the type of bone that may be associated with the various changes in the sensed voltage. The change or different voltages may be predetermined. As discussed above, the bone of the vertebrae 36 may include a cortical portion 404*a*, a cancellous portion 408, and a second cortical portion 404*b*. As the tool tip 32*t* engages the different types of bone, as illustrated in the row 520, the voltage sensed at the motor sensor 220 may alter as illustrated in the graph 500. The sensor 220 may send a signal to the motor controller 144 to assist in determining or altering an operation of the motor drill 20. Accordingly, the voltage sensed at the motor sensor 220 may assist in operating or determining the operation of the drill 20.

Turning reference to FIGS. 7A, 7B, 7C, and 7D, the drill 20 may be operated, again, to engage or interact with a selected portion of the subject, such as the vertebrae 36, including the facet 150. Again, the spinal cord 162 may generally be near or at the vertebrae 36. The spinal cord 162, for example, may again be identified as an avoidance space or region. Further, extending from the spinal cord 162 may be various nerve bundles 166. The nerve bundles 166 may also be defined as avoidance spaces or volumes in a manner similar to that discussed above regarding the spinal cord 162. Again, the avoidance spaces may be identified and displayed on the display screen 82 and/or sent and recalled for various purposes, such as operation of the drill 20.

As discussed above, therefore, the avoidance spaces, which may be defined relative to or by the spinal cord 162 and/or nerves 166 relative thereto, and may be used for selecting operation of the drill 20. The tracking device 98, 98' may be associated with the drill 20, such as connected thereto. Thus, the navigation system or tracking system may track and determine the position of the drill 20 and the tool 32 related thereto. The tool 32 may include a selected tool, such as a burr or router portion, to remove a selected portion of the anatomy, such as a portion of the facet 150. The tool 132 may remove the facet material generally by moving in the direction of arrow 540. By moving in the direction of arrow 540 the tool 32, including the tool tip 32*t*, may remove a selected portion of the facet 150.

In addition to the tracking device 98, 98' associated with the drill 20, additional sensors may be associated with the drill 20. As discussed above, the motor sensor 220 may be provided to sense the operation or voltage applied by the motor and/or feedback to the motor. In addition to the sensor, or alternatively to a motor sensor 220 and/or the tracking device 98, 98', the electrical conductivity or integrity sensor 234 may be provided near the tool 32. The conductivity sensor 234 may include a nerve integrity monitoring device sensor that may sense a signal provided through the spinal cord 162 and/or other nerve pathways, such as the nerves 166. The conductivity sensor 234 may include those included or similar to those included with the NIM® monitoring systems sold by Medtronic, Inc. Accordingly, the integrity sensor 234 may sense a signal and transmit the signal to an appropriate location for processing, such as the drill motor controller 144.

As illustrated in FIG. 7A, for example, the tool 32, associated with the drill 20, may have its location tracked and determined with the tracking device 98, 98'. At an initial position 550, the tool 32 may rotate at a selected speed, such as generally in the direction of arrow 560, generally or substantially around the axis 400 or a line generally parallel thereto. The drill 20 may be moved generally in the direction of arrow 540 to initiate or remove a selected portion of the bone, such as of the vertebrae 36. The tool 32 may continue to move generally in the direction of arrow 540, which may move the tool 32 nearer to the nerve 166. Again, the position of the tool 32 may be tracked or determined based upon the tracking device 98, 98'.

At a selected second distance, such as a distance 564, the tool 32 may still rotate generally in the entire rotation direction illustrated by the arrow 560, but may have an altered speed, based upon the operation of the drill according to the various recalled parameters, such as those discussed above in the operation subroutine 340 and in the motor controller 144. Again, the operation of the drill 20 and the associated tool 32 may be based upon various determinations. The predetermined operation parameters may be based on the determined proximities, such as a proximity to the nerve 16, the determined kinematics such as determined in block 260, and the like. This may be determined based upon tracking the tracking device 98 over time. Accordingly, if the tool 32 is moving at a selected speed, such as greater than 1 mm or 1 centimeter per minute, at the distance 564, the rotational speed in the direction of the arrow 560 may be altered, such as reduced. Accordingly, the speed and direction of movement of the tool 32 may be used to assist in selecting the parameters for controlling the drill 20 at a selected time.

Turning reference to FIG. 7C, the integrity sensor 234 may be near the nerve 166. At a selected proximity, the integrity sensor 234 may sense the signal through the nerve 166. The integrity sensor signal through the integrity sensor 234 and/or the position determined with the tracking device 98, 98' may be used to determine a change in an operation parameters of the drill 20. At the selected distance and/or signal sensing by the integrity sensor 234 the operation of the tool 32 may be changed to an oscillation, such as illustrated by the two arrows 580 and 584, generally or substantially around the axis 400 or a line generally parallel thereto. Again, the oscillation may be any selected oscillation, such as generally in an arc in selected directions, such as an arc of about 50 degrees to about 140 degrees, such as including the arc 586 and 588. Thus, the various inputs, including proximities determined in block 250, kinematics determined in block 260, and contacts determined in block 270 may be used to assist in determining or selecting an operation of the drill 20 for the tool 32. Further, the drill 20 may be operated based upon the inputs selected by the user, and the various inputs of one or more of the sensor as discussed above.

As illustrated in FIG. 7D, the integrity sensor 234 may sense contact or emanate contact with the nerve 166. The integrity sensor 234, therefore, may transmit a signal based thereon and a determination that the tool 32 should be stopped may be determined. Thus, rotation of the tool 32 may be eliminated. Again, the integrity sensor 234 may sense contact or substantially near contact with the nerve 166. Additionally, the tracked position of the drill 20 may be made with the tracked device 98, 98', as discussed above. The various inputs may be used to determine operation of the drill 20 according to the process 310, including the operational process portion 340, and the various inputs based upon the controller 144 execution thereof, as also discussed above.

Accordingly, various sensor may be provided to sense operation of the drill 20 and/or movement of the drill 20 or the tool 32. The various inputs may be used to determine various parameters relative to the tool 32, such as contacts, proximities, and kinematics to assist in selecting and/or determining an operation of the drill 20. The operation parameters may be based on the position determined with a navigation system, such as with the tracking device 98, 98', and one or more other sensor inputs may also be provided. As discussed above, the motor sensor 220, the integrity sensor 234, and other appropriate sensors may be provided to provide input for execution of selected instructions to operate the drill 20.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by a special purpose computer created by configuring a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C#, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

A processor or module or 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A system to control operation of a drill, comprising:
a sensor configured to sense at least one operation of a motor of the drill and transmit a sensor signal based thereon;
a processor module configured to receive the sensor signal and execute instructions to operate the drill and alter an operation parameter of the drill based at least on the sensor signal;
wherein the sensor signal includes at least a first signal and a second signal;
wherein the operation of the drill includes at least a full rotation of the drill about a drill axis of rotation when the first signal is received and an oscillation of the drill about the drill axis of rotation where the drill will rotate a selected amount in a first direction about the drill axis of rotation and then rotate a selected amount in a second opposite direction about the drill axis of rotation when the second signal is received.

2. The system of claim 1, wherein the sensor includes a voltage sensor configured to sense a back voltage to a motor of the drill;
wherein the first signal is a first back voltage and the second signal is a second back voltage.

3. The system of claim 1, further comprising:
a tracking device configured to be associated with the drill;
a navigation system configured to determine a pose of the drill based on tracking the tracking device; and
wherein the processor module is configured to execute further instructions to alter the operation parameter based on the determined pose of the drill;
wherein the operation parameter of the drill is selected based on both (i) the first sensor signal or the second sensor signal and (ii) the determined pose.

4. The system of claim 3, further comprising:
a boundary determination system configured to determine a boundary in an image;
wherein the operation parameters are altered based on the determined position of the drill relative to the boundary.

5. The system of claim 4, wherein the boundary determination system comprises:
a display device configured to display an image; and
an input system configured to allow an input of a user regarding a boundary of at least a portion of displayed in the image.

6. The system of claim 3, further comprising:
an imaging system configured to image the subject; and
a boundary determination system configured to determine a boundary within the image.

7. The system of claim 6, wherein the boundary determination system includes a user input to select at least a seed portion.

8. The system of claim 3, wherein the boundary determination system includes an image segmentation system configured to segment images of the subject.

9. The system of claim 1, wherein the oscillation parameter is selected at a distance relative to a boundary in the image.

10. The system of claim 1, further comprising:
an auxiliary sensor operable to sense an electrical signal transmitted through a nerve;
wherein the processor module is further configured to receive an auxiliary sensor signal from the auxiliary sensor.

11. A system to control operation of a drill, comprising:
a sensor configured to sense an electrical signal transmitted through a nerve in a subject and transmit a sensor signal based thereon;
a processor module configured to receive the sensor signal and execute instructions to operate the drill and alter an operation parameter of the drill based on the sensor signal;
wherein the sensor signal includes at least a first signal and a second signal;
wherein the operation of the drill includes at least a full rotation the drill about a drill axis of rotation when the first signal is received and an oscillation of the drill about the drill axis of rotation where the drill will rotate a selected amount in a first direction about the drill axis of rotation and then rotate a selected amount in a second opposite direction about the drill axis of rotation when the second signal is received.

12. The system of claim 11, wherein the first signal includes no nerve signal and the second signal includes a nerve signal.

13. The system of claim 12, further comprising:
a tracking device configured to be associated with the drill;
a navigation system configured to determine a pose of the drill based on tracking the tracking device; and
wherein the processor module is configured to execute further instructions to alter the operation parameter based on the determined pose of the drill;

wherein the operation parameter of the drill is selected based on both (i) the first sensor signal or the second sensor signal and (ii) the determined pose.

14. The system of claim 13, further comprising:
a boundary determination system configured to determine a boundary in an image;
wherein the operation parameters are altered based on the determined pose of the drill relative to the boundary.

15. The system of claim 14, wherein the boundary determination system comprises:
a display device configured to display an image; and
an input system configured to allow an input of a user regarding a boundary of at least a portion of displayed in the image.

16. The system of claim 15, further comprising:
an imaging system configured to image the subject; and
a boundary determination system configured to determine a boundary within the image.

17. The system of claim 16, wherein the boundary determination system includes a user input to select at least a seed portion.

18. The system of claim 17, wherein the oscillation parameter is selected at a distance relative to the boundary in the image.

19. A method to control operation of a drill, comprising:
determining a sensor signal from a sensor configured to sense a condition relative to the drill;
determining a pose of the drill with a navigation system configured to determine a pose of the drill; and
controlling an operation of the drill according to a selected operation parameter, wherein controlling the operation includes executing instructions with a processor module to alter the operation parameter of the drill based on both (i) the determined pose of the drill and (ii) the sensor signal;
wherein controlling the operation of the drill includes at least a full rotation of the drill about a drill axis of rotation and an oscillation of the drill about the drill axis of rotation where the drill will rotate a selected amount in a first direction about the drill axis of rotation and then rotate a selected amount in a second opposite direction about the drill axis of rotation.

20. The method of claim 19, wherein determine the sensor signal includes at least one of:
an electrical signal transmitted through a nerve in a subject and transmit a sensor signal based thereon, or
at least one operation of a motor of the drill.

21. The method of claim 20, further comprising:
determining a boundary in an image;
wherein controlling the operation of the instrument is based on both (i) the determined pose of the instrument relative to the boundary and (ii) the sensor signal.

22. The method of claim 21, further comprising:
displaying the image; and
inputting a user selection regarding the boundary of at least a portion of displayed in the image.

23. The method of claim 22, wherein determining the boundary within the image includes receiving a user input to select at least a seed portion.

24. The method of claim 21, wherein the oscillation of the drill is selected at a distance relative to the determined boundary in the image.

* * * * *